United States Defensive Publication [19] (H) [11] T960,003

Innes et al. [43] July 5, 1977

[54] ALLEVIATION OF TISSUE DAMAGE WITH BIS(SUBSTITUTEDPHENYL)MERCAPTOLES

[76] Inventors: Ian R. Innes, 575 Elm St.; William J. Davidson, 1286 Paterson St., both of Winnipeg, Manitoba, Canada

[21] Appl. No.: 686,357

[22] Filed: May 14, 1976

[51] Int. Cl.[2] ..... A61K 31/10

[52] U.S. Cl. ..... 424/337

[57] ABSTRACT

Tissue damage alleviative effects are obtained by administration of a bis(substitutedphenyl)mercaptole, such as probucol, to animals. Tissue protective or recuperative effects are obtained, for example, in cardiac hepatic, uterine and kidney tissue subject to myopathy or histopathological injury by oral or parenteral administration of mercaptole compounds.

21 Claims, No Sheets Drawing,

25 Pages Specification

The file of this unexamined application may be inspected and copies thereof may be purchased (849 O.G. 1221, Apr. 9, 1968).